US011854122B2

(12) United States Patent
Grobshtein et al.

(10) Patent No.: US 11,854,122 B2
(45) Date of Patent: *Dec. 26, 2023

(54) SYSTEMS AND METHODS FOR IMAGE QUALITY ENHANCEMENT FOR MULTI-HEAD CAMERA

(71) Applicant: General Electric Company, Schenectady, NY (US)

(72) Inventors: Yariv Grobshtein, Haifa (IL); Michal Maria Merman, Nesher (IL); Shai Wald, Haifa (IL); Raz Carmi, Haifa (IL)

(73) Assignee: General Electric Company, Schenectady, NY (US)

( * ) Notice: Subject to any disclaimer, the term of this patent is extended or adjusted under 35 U.S.C. 154(b) by 165 days.

This patent is subject to a terminal disclaimer.

(21) Appl. No.: 17/486,628

(22) Filed: Sep. 27, 2021

(65) Prior Publication Data

US 2022/0012925 A1   Jan. 13, 2022

Related U.S. Application Data

(63) Continuation of application No. 16/183,283, filed on Nov. 7, 2018, now Pat. No. 11,151,758.

(51) Int. Cl.
| | |
|---|---|
| *G06T 11/00* | (2006.01) |
| *A61B 6/00* | (2006.01) |
| *A61B 6/03* | (2006.01) |

(52) U.S. Cl.
CPC ............ *G06T 11/003* (2013.01); *A61B 6/037* (2013.01); *A61B 6/4476* (2013.01); *A61B 6/469* (2013.01)

(58) Field of Classification Search
CPC .................................................... G06T 11/003
See application file for complete search history.

(56) References Cited

U.S. PATENT DOCUMENTS

| | | | |
|---|---|---|---|
| 6,140,650 A | 10/2000 | Berlad | |
| 6,239,438 B1 | 5/2001 | Schubert | |
| (Continued) | | | |

FOREIGN PATENT DOCUMENTS

| | | |
|---|---|---|
| WO | 2008135994 A2 | 11/2008 |
| WO | 2009036078 A2 | 3/2009 |

OTHER PUBLICATIONS

PCT Search Report and Written Opinion issued in connection with corresponding Application No. PCT/IL2014/050848 dated Feb. 5, 2015.

(Continued)

*Primary Examiner* — Joseph M Santos Rodriguez
(74) *Attorney, Agent, or Firm* — The Small Patent Law Group, LLC; Dean D. Small (57) ABSTRACT

A nuclear medicine (NM) multi-head imaging system is provided that includes a gantry, detector units, and at least one processor. The gantry defines a bore. The detector units are mounted to the gantry and configured to rotate as a group with the gantry around the bore in rotational steps, with each detector unit configured to sweep about a corresponding axis and acquire imaging information while sweeping about the corresponding axis. The at least one processor is coupled to the detector units and configured to determine a region of interest (ROI) of the object to be imaged; determine a sweeping configuration based on the size of the ROI; determine a rotational movement configuration for the gantry using the determined sweeping configuration; and control the gantry and the set of detector units to utilize the determined rotational movement and sweeping configurations during acquisition of imaging information.

20 Claims, 8 Drawing Sheets

(56) References Cited

U.S. PATENT DOCUMENTS

| | | | |
|---|---|---|---|
| 6,388,244 B1 | 5/2002 | Gagnon | |
| 6,535,229 B1 | 3/2003 | Kraft | |
| 6,748,044 B2 | 6/2004 | Sabol et al. | |
| 6,943,355 B2 | 9/2005 | Schwartz et al. | |
| 7,026,623 B2 | 4/2006 | Oaknin et al. | |
| 7,381,959 B2 | 6/2008 | Manjeshwar et al. | |
| 7,671,331 B2 | 3/2010 | Hefetz | |
| 8,280,124 B2 | 10/2012 | Dichterman et al. | |
| 8,492,725 B2 | 7/2013 | Zilberstein et al. | |
| 2002/0191828 A1 | 12/2002 | Colbeth et al. | |
| 2005/0145797 A1 | 7/2005 | Oaknin et al. | |
| 2006/0108532 A1 | 5/2006 | Ohana et al. | |
| 2007/0018108 A1 | 1/2007 | Kitamura | |
| 2008/0092074 A1 | 4/2008 | Cohen | |
| 2009/0070121 A1 | 3/2009 | Leonelli et al. | |
| 2012/0108948 A1 | 5/2012 | Jansen et al. | |
| 2012/0205542 A1 | 8/2012 | Goedicke et al. | |
| 2013/0168567 A1 | 7/2013 | Wartski et al. | |
| 2014/0126793 A1 | 5/2014 | Ahn et al. | |
| 2017/0014096 A1 | 1/2017 | Bouhnik et al. | |

OTHER PUBLICATIONS

Meikle et al., "Accelerated EM reconstruction in total-body PET: potential for improving tumour detectability," 1994, Physics in Medicine and Biology, vol. 39, pp. 1689-1704.

Park et al., "Performance of a high-sensitivity dedicated cardiac SPECT scanner for striatal uptake quantification in the brain based on analysis of projection data," Med. Phys. 40 (4), Apr. 2013.

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

SYSTEMS AND METHODS FOR IMAGE QUALITY ENHANCEMENT FOR MULTI-HEAD CAMERA

CROSS-REFERENCE TO RELATED APPLICATIONS

This application is a continuation of U.S. patent application Ser. No. 16/183,283, filed on Nov. 7, 2018, now allowed. The entire disclosure of the Ser. No. 16/183,283 application is incorporated herein by reference.

BACKGROUND

The subject matter disclosed herein relates generally to medical imaging systems, and more particularly to radiation detection systems.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having several individual detectors distributed about the gantry. Each detector may pivot or sweep to provide a range over which the detector may acquire information that is larger than a stationary field of view of the detector. Focus-based acquisition may improve image quality in a focused region. Obtaining good image quality of all features in a focused region requires sufficient time for acquisition of all projections observing the region, and failure to acquire sufficiently wide coverage of a region of interest may result in distortions due to noise, for example if edge projections are not included in a focused region. However, on the other hand, increasing the width of coverage may result in an overall increase in scan time.

BRIEF DESCRIPTION

In accordance with an embodiment, a nuclear medicine (NM) multi-head imaging system is provided that includes a gantry, plural detector units, and at least one processor. The gantry defines a bore configured to accept an object to be imaged, and is configured to rotate about the bore. The plural detector units are mounted to the gantry and configured to rotate as a group with the gantry around the bore in rotational steps. Each detector unit is configured to sweep about a corresponding axis and acquire imaging information while sweeping about the corresponding axis. The at least one processor is operably coupled to at least one of the detector units, and is configured to determine a region of interest (ROI) of the object to be imaged; identify a set of detector units from the plural detector units mounted to the gantry; for the identified set of detector units, determine a sweeping configuration that results in a predetermined percentage of projection pixels receiving information from the ROI; determine a rotational movement configuration for the gantry using the determined sweeping configuration; and control the gantry and the set of detector units to utilize the determined rotational movement and sweeping configurations during acquisition of imaging information. It may be noted, for example, that in various embodiments, the order of various steps may be revised. For example, the rotational configuration may be determined before the sweeping configuration, or the determinations may be performed alternately in an iterative fashion.

In accordance with another embodiment, a nuclear medicine (NM) multi-head imaging system is provided that includes a gantry, plural detector units, and at least one processor. The gantry defines a bore configured to accept an object to be imaged, and is configured to rotate about the bore. The plural detector units are mounted to the gantry and configured to rotate as a group with the gantry around the bore in rotational steps, with each detector unit configured to sweep about a corresponding axis and acquire imaging information while sweeping about the corresponding axis. The at least one processor operably coupled to at least one of the detector units, and is configured to determine a region of interest (ROI) of the object to be imaged; for at least one of a number of different total rotational step combinations, determine gaps resulting between detector views for each rotational step combination; determine a number of rotational steps to be used based on the gaps; and control the gantry and the set of detector units using the determined number of rotational steps during acquisition of imaging information.

In accordance with another embodiment, a method is provided for acquiring imaging information with a nuclear medicine (NM) multi-head imaging system. The system includes a gantry and plural detector units. The gantry defines a bore configured to accept an object to be imaged, and is configured to rotate about the bore. The plural detector units are mounted to the gantry and configured to rotate as a group with the gantry around the bore. Each detector unit is configured to sweep about a corresponding axis and acquire imaging information while sweeping about the corresponding axis. The method includes determining a region of interest (ROI) of the object to be imaged. The method also includes identifying a set of detector units from the plural detector units mounted to the gantry. Further, the method includes, for the identified set of detector units, determining a sweeping configuration that results in a predetermined percentage of projection pixels receiving information from the ROI. Also, the method includes determining rotational movement configuration for the gantry using the determined sweeping configuration. The method further includes controlling the gantry and the set of detector units to utilize the determined rotational movement and sweeping configurations during acquisition of imaging information.

DETAILED DESCRIPTION

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for improving image quality. Various embodiments balance an increased width in coverage of a region of interest (ROI) with gantry rotational positions or steps to allow use of relatively wide coverage while reducing or optimizing a relatively low number of focus views. Accordingly, scan time may be reduced while maintaining image quality. Various embodiments provide improved scan efficiency using a flexible scan design, in which primary detectors cover the ROI using more time for focused acquisition of the ROI, while remaining detectors are utilized to provide more scanning time on background acquisition. Further, various embodiments provide for efficient planning of scans including selection of a number of rotational steps or positions of a gantry, and/or shifts or offsets for rotational steps or positions of a gantry.

A technical effect of at least one embodiment includes improved image quality. A technical effect of at least one embodiment includes reduced acquisition time and/or reduced injected dose. A technical effect of at least one embodiment includes improved providing of adequate coverage of a ROI. A technical effect of at least one embodiment includes improved positioning of detectors along rotational steps taken by a gantry.

Figure 1:
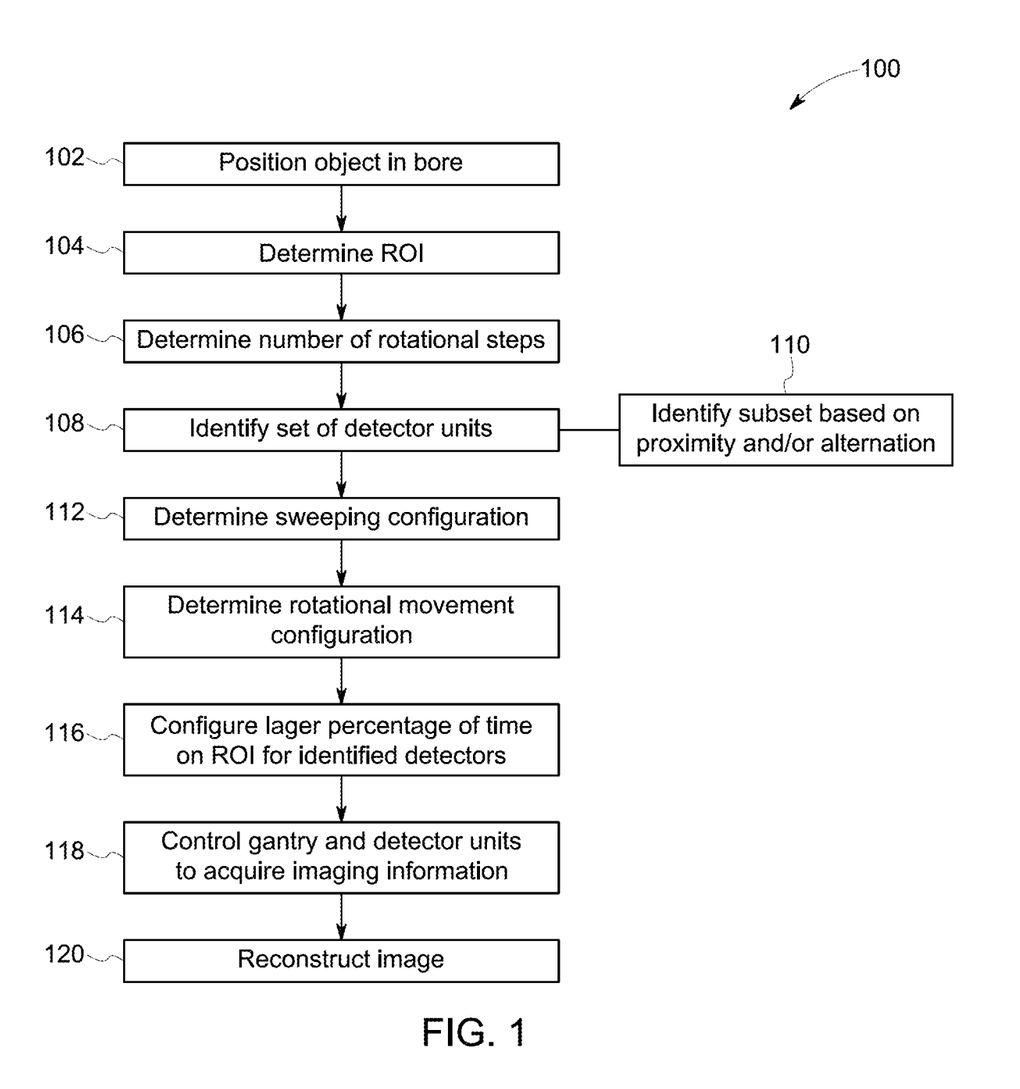
FIG. 1 provides a flowchart of a method, according to an embodiment.

FIG. 1 provides a flowchart of a method 100 for controlling detector heads of a multi-head imaging system and/or reconstructing an image using focused and non-focused (or background) imaging information (including edge and interior information) acquired with detector heads of a multi-head imaging system in accordance with various embodiments. The method 100 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. It may be noted, for example, that in various embodiments, the order of various steps may be revised. For example, the rotational configuration may be determined before the sweeping configuration, or the determinations may be performed alternately in an iterative fashion. In various embodiments, portions, aspects, and/or variations of the method 100 may be able to be used as one or more algorithms to direct hardware (e.g., one or more aspects of a processing unit discussed herein) to perform one or more operations described herein.

At 102, an object to be imaged is positioned in the bore of a NM imaging system (e.g., system 1000 discussed herein). In various embodiments, the NM imaging system includes a gantry and plural detector units attached to the gantry. The gantry defines a bore in which the object to be imaged (e.g., human patient) is disposed. The gantry rotates about the bore, with the plural detector units mounted to the gantry and configured to rotate as a group with the gantry around the bore in rotational steps. Also, each detector unit is configured to sweep about a corresponding axis and acquire imaging information while sweeping about the corresponding axis.

At 104, a region of interest (ROI) of the object to be imaged is determined. Generally, the ROI corresponds to or includes a portion of the object that is of particular diagnostic interest. For example, the ROI may be determined to include an organ (or organs) that are to be evaluated by a scan, and may include a buffer region around the organ (or organs) to insure complete inclusion of the organ (or organs) in the ROI. In some embodiments, the ROI may be specified by a user (e.g., via inputting a boundary of the ROI via a touchscreen or other input device). In some embodiments, the ROI may be located automatically by one or more processing units from an attenuation map and/or anatomical landmarks, for example.

Figure 2:
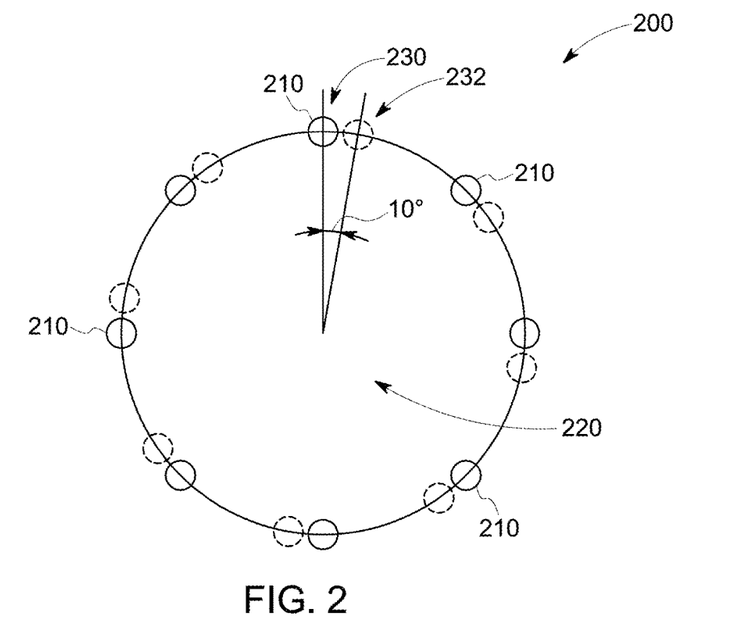
FIG. 2 illustrates an example gantry having 8 detector units configured to move with the gantry in rotational steps according to an embodiment.

At 106, a total number of rotational steps to be taken by the gantry is determined. FIG. 2 illustrates an example gantry 200 having 8 detector units 210 disposed about a bore 220. In a first rotational step 230, shown in solid lines, the detectors 210 are at a first position. In a second rotational step 232, the detectors 210 are in a second position, shifted ten degrees clockwise from the first position. Additional rotational steps may be employed in various embodiments, for example, up to the point at which a given detector is positioned where its adjacent detector was originally positioned.

Figure 3:
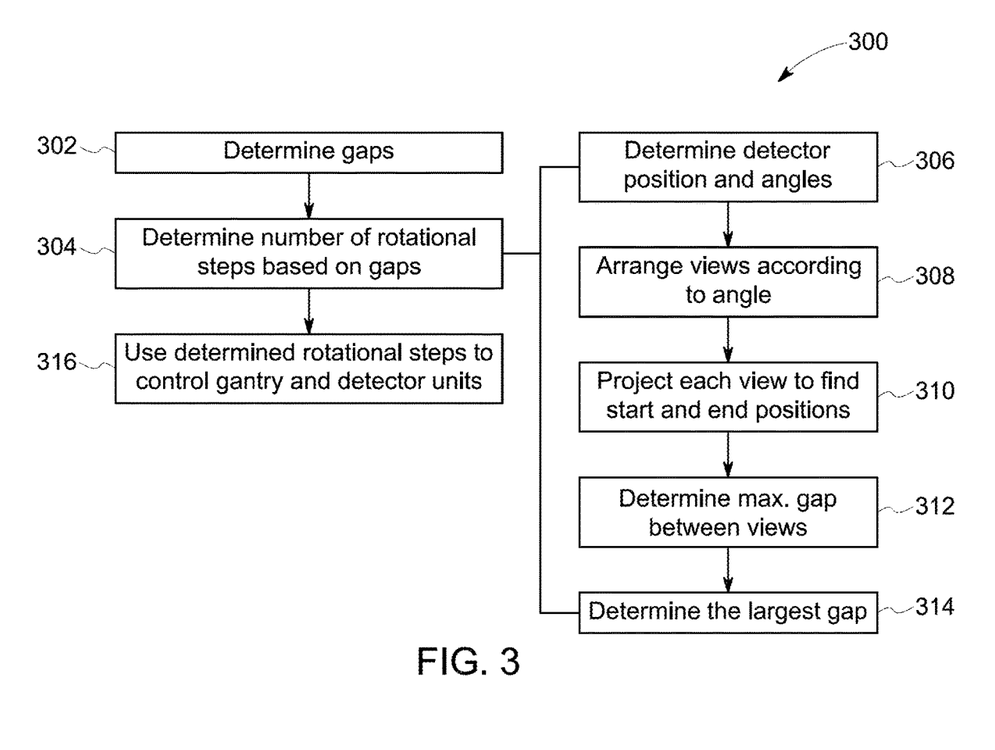
FIG. 3 provides a flowchart of a method, according to an embodiment.

Various techniques may be employed to determine the total number of rotational steps in various embodiments. For example, FIG. 3 provides a flowchart of a method 300 for determining the number of rotational steps. It may be noted that the method 300 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be able to be used as one or more algorithms to direct hardware (e.g., one or more aspects of a processing unit discussed herein) to perform one or more operations described herein.

Figure 4:
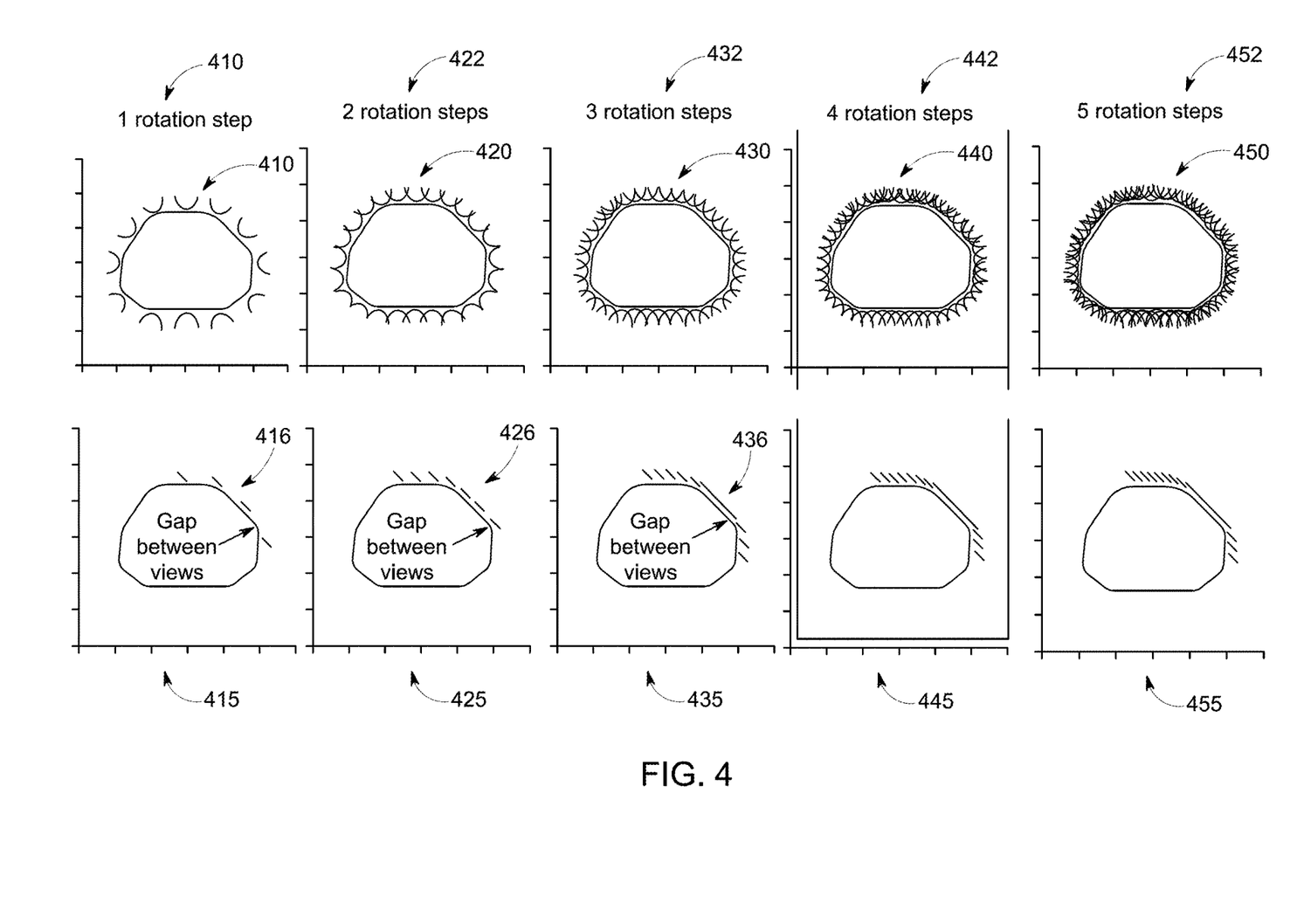
FIG. 4 illustrates example rotational steps and corresponding gaps between views, according to an embodiment.

At 302, gaps (gaps that result between detector views) are determined for at least one of a number of different total rotational step combinations. For each rotational step of the gantry, the detectors mounted to the gantry may have gaps therebetween for each view angle. For example, FIG. 4 illustrates example rotational steps and corresponding gaps between views. As seen in FIG. 4, at the first rotational step 410 (e.g., an uppermost detector located at a 12:00 position), for any given viewing angle, gaps may appear between the views provided by adjacent detectors. For example, at about a 46 degree viewing angle, view 415 depicts the gaps 416 between adjacent detectors for the first rotational step 410.

As seen in FIG. 4, second rotational step combination 420 includes the detector positions provided by the first rotational step 410 along with a second rotational step 422, with each detector moved one increment in the clockwise direction from the first rotational step 410 to the second rotational step 422. View 425 depicts the gaps 426 between the detector views at the 46 degree viewing angle for both the first and second rotational steps combined. As seen in FIG. 4, the gaps for the rotational step combination 420 are smaller than those for the first rotational step 410 alone.

Similarly, third rotational step combination 430 includes the detector positions provided by the first rotational step 410 and second rotational step 422 along with a third rotational step 432, with each detector moved one increment in the clockwise direction from the second rotational step 422 to the third rotational step 432. View 435 depicts the gaps 436 between the detector views at the 46 degree viewing angle for the first, second, and third rotational steps combined. Also, fourth rotational step combination 440 includes the detector positions provided by the first rotational step 410, second rotational step 422, third rotational step 432, along with a fourth rotational step 442, with each detector moved one increment in the clockwise direction from the third rotational step 432 to the fourth rotational step 442. View 445 depicts the gaps between the detector views at the 46 degree viewing angle for the first, second, third, and fourth rotational steps combined (in the illustrated example, there are no gaps in view 445). Likewise, fifth rotational step combination 450 includes the detector positions provided by the first rotational step 410, second rotational step 422, third rotational step 432, and fourth rotational step 442, along with a fifth rotational step 450 with each detector moved one increment in the clockwise direction from the fourth rotational step 442 to the fifth rotational step 452. View 445 depicts the gaps between the detector views at the 46 degree viewing angle for the first, second, third, fourth, and fifth rotational steps combined.

As seen in FIG. 4, as more rotational steps are added to the combination, the gaps become smaller until the fourth rotational step combination 440, at which point the gaps are eliminated. Accordingly, any additional rotational steps are unnecessary and would result in unnecessary additional scanning time.

Returning to FIG. 3, at 304, a number of rotational steps to be used is determined based on the gaps. For example, the number of rotational steps may be selected to ensure a minimum average gap size, or as another example, to ensure a minimum size of the largest gap. In some embodiments, the number of rotational steps is determined to satisfy a predetermined maximum threshold gap size (e.g., the size of the largest gap present). For example, with reference to FIG. 4, if the predetermined threshold gap size is zero, in the illustrated example, the fourth rotational step combination 440 would provide the desired zero gap and fourth rotational steps would be selected. In other embodiments, the maximum threshold gap size may be larger than zero and the third rotational step combination 430, for example, may provide acceptable results.

It may be noted that in various embodiments, the gap may be determined iteratively. For example, gaps resulting for an initial number of rotational steps may be determined and compared to a threshold. If the threshold is satisfied, the initial number of rotational steps may be used as the number of rotational steps used to control the gantry and detectors during imaging. However, if the threshold is not satisfied using the initial number of rotational steps, the number of rotational steps may be increased. For example, the number of rotational steps may be iteratively increased by one until the resulting steps satisfy the threshold.

Additionally or alternatively, in various embodiments, a scan of the ROI may be acquired (e.g., a preliminary scan that includes enough information to determine a general outline or boundary of the ROI), and/or a boundary of the ROI may be provided via a user input. Next a size of the ROI may be determined. It may be noted that the size of the ROI may include values in 2 or 3 dimensions taken at various portions of the ROI, so that the size also indicates the shape of the ROI. The number of rotational steps may be determined based on the size of the ROI. For example, a predetermined relationship between ROI size and number of rotational steps may be utilized. In some embodiments, a lookup table may be used. For example, the ROI may be approximated as an ellipse having a defined long axis and a defined short axis. The ellipse representing the ROI may then be compared to a listing of ellipses with known corresponding numbers of appropriate rotational steps, and the number of rotational steps for the listed ellipse that most closely matches the ellipse representing the ROI may be used. As another example, the smallest listed ellipse that completely bounds the ROI may be identified, with the number of rotational steps for the smallest bounding listed ellipse used as the number of rotational steps. It may be noted that, in some embodiments, the number of rotational steps determined based on the size of the ROI may be used as the initial estimate of rotational steps of an iterative process as discussed above. It may be noted that, in various embodiments, the use of look-up tables and predetermined ellipse sizes need not necessarily be limited to use with ROI's and/or focused scans. For example, the use of look-up tables and predetermined ellipse sizes may be used for an entire body and/or for unfocused scans.

Figure 5:
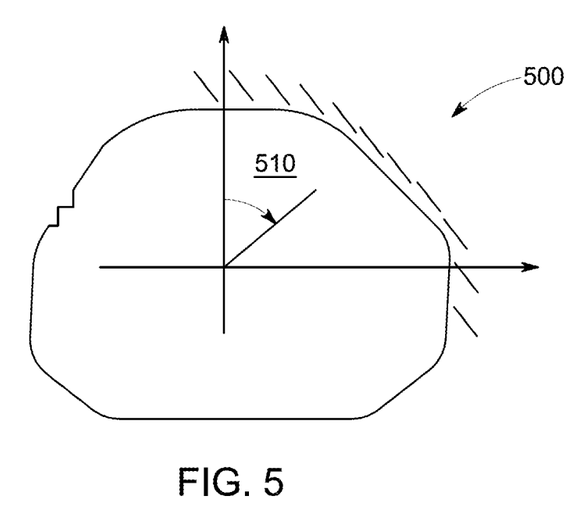
FIG. 5 depicts an example group of detector views that are at the same view angle, according to an embodiment.

Various substeps may be employed to determine the number of rotational steps. For example, in the example embodiment depicted in FIG. 3, at 306, detector positions and angles are determined for all view provided by the detectors for the rotational step combination. Each view provided by each detector at each rotational step may be determined. At 308, the detector views are arranged in bins according to view angle. For example, FIG. 5 depicts an example group 500 of detector views that are at the same view angle 510 that would be binned together at 308.

Figure 6:
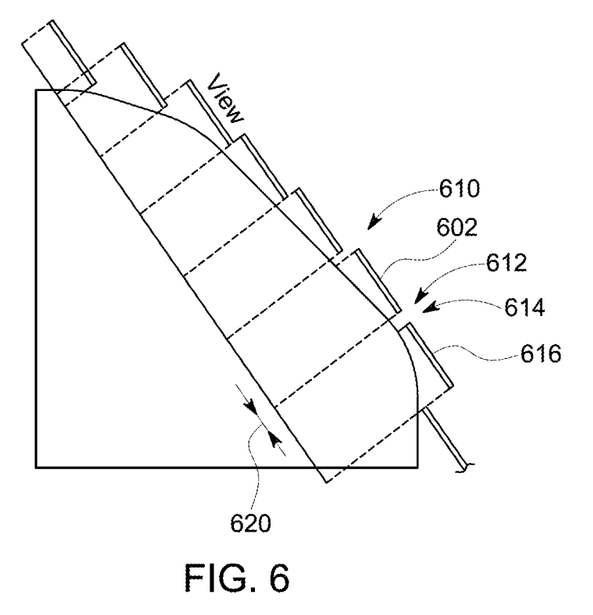
FIG. 6 depicts an example group of detector views.

At 310, each detector view of each bin is projected along the view angle to find a start and end position for each corresponding detector. For example, FIG. 6 depicts an example group 600 of detector views. As seen in FIG. 6, example detector 602 has a start position 610 and an end position 612. At 312, the maximum gap between projected views is determined. For example, the gap may be determined by the distance between the start and end positions of adjacent projected views from 310. As seen in the example of FIG. 6, the maximum gap is the gap 620 between the end position 612 of detector 610 and the start position 614 of adjacent detector 616. At 314 of the illustrated example, the largest gap of the maximum gaps (e.g., the group of individual maximum gaps from each bin) is determined, and used in determining the number of rotational steps.

With the number of rotational steps determined, at 316, the gantry and detector units are controlled using the determined number of rotational steps during acquisition of imaging information.

Returning to FIG. 1, at 108, a set of detector units is identified from the plural detector units mounted to the gantry. In some embodiments, the set of detector units is all available detector units, while in other embodiments the set of detector units is a subset of all available detector units. For example, the set of detector units selected may be a set of detector units best suited for imaging the ROI, while other remaining detector units not selected are better suited for imaging background aspects of the object being imaged, and/or may be utilized to acquire information of a more narrow field of view including the ROI than the selected set of detector units. In the illustrated embodiment, at 110, the detectors of the subset are identified based on at least one of a proximity to the ROI or corresponding attenuation to the detector units. For example, those detectors disposed closest to the ROI may be used to more efficiently provide information on the ROI. Similarly, those detectors having less attenuation between the detector and the ROI may be used to more efficiently provide information on the ROI.

At 112, for the identified set of detector units, a sweeping configuration is determined. In various embodiments, the sweeping configuration is determined to result in a predetermined percentage of available pixels (e.g., a percentage of projection pixels as discussed in connection with FIG. 7 below) receiving information from the ROI. The sweeping configuration in various embodiments specifies where each detector sweeps (e.g., defines a sweeping boundary for each detector of the subset) at a given rotational step of the gantry (or at each rotational step of the gantry when multiple gantry rotational steps are utilized). The sweeping boundary, for example, may specify two view angles bounding the sweep range. The sweeping configuration in various embodiments may also specify a sweeping speed. It may be noted that the predetermined percentage of pixels may vary among detector units within the identified set and/or outside of the identified set.

Figure 7:
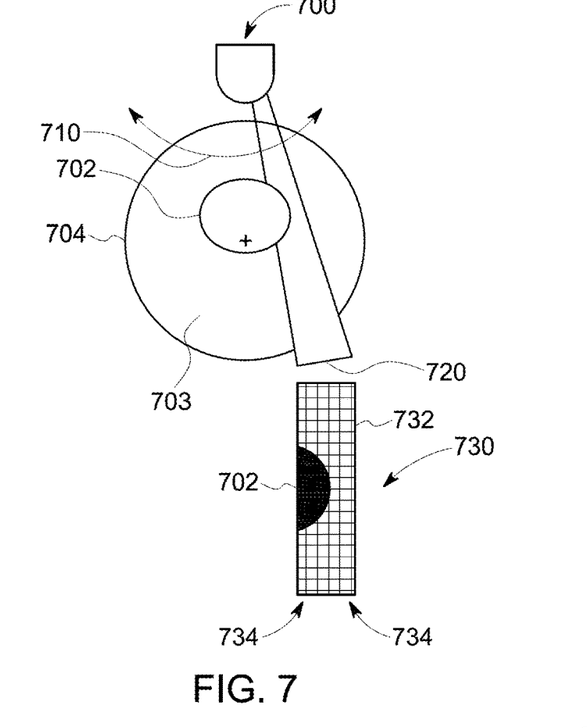
FIG. 7 illustrates an example sweep range boundary, according to an embodiment.

FIG. 7 illustrates and example sweep range boundary (e.g., boundary of a range of view angles over which a given detector sweeps during acquisition of imaging information). As seen in FIG. 7, a detector unit 700 is used to image an ROI 702 of an object 704 (e.g., human patient). As depicted in FIG. 7, the detector unit 700 is at an edge of a sweep boundary along a sweeping direction 710, with a corresponding field of view 720 that includes part of the ROI 702 and part of a background portion 703 of the object 704. As seen in projection 730 of pixels 732, a percentage of pixel columns 734 collect information regarding the ROI 702. The sweeping configuration at 112 in various embodiments is set so that the percentage of pixel columns collecting information at the sweep boundary or edge of sweeping zone is a predetermined percentage (e.g., 50% of pixel columns receive information of the ROI at the sweep boundary). For wider coverage (e.g., to insure adequate coverage of the ROI by selected detectors) a relatively low percentage may be utilized, while a higher percentage may be utilized to provide more narrow coverage.

Figure 8:
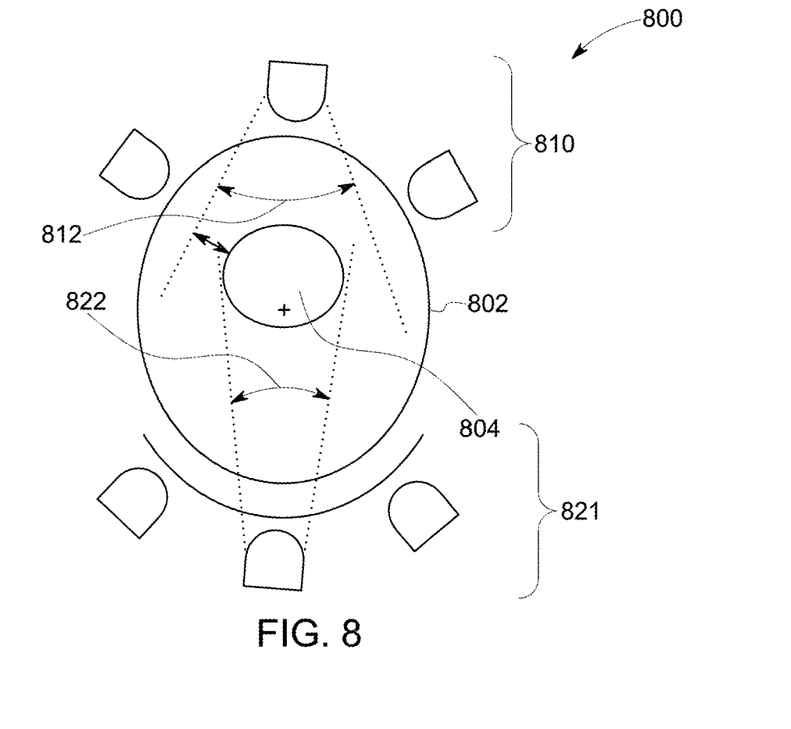
FIG. 8 illustrates an example detector system, according to an embodiment.

FIG. 8 illustrates an example detector system 800 having a first set of detector units 810 (e.g., detector units identified at 108) and a second set of detector units 820 (e.g., detector units not identified at 108) being used to image an object 802 having an ROI 840. The first set of detector units 810 have a relatively wide range of coverage 812. Such a wide range of coverage helps insure adequate coverage of the ROI for improved image quality over the entire ROI. In various embodiments such a wide range of coverage may be selected only for a set of detectors (e.g., set 810) depending on proximity to the ROI 804 and/or attenuation considerations. For the remaining detectors (second set of detector units 820), a narrower range 822 may be employed, thereby, for example, adding flexibility to scan design and required scanning time.

Returning to FIG. 1, at 114, a rotational movement configuration is determined for the gantry, using the determined sweeping configuration. The rotational movement configuration in various embodiments specifies how and when the gantry rotates during imaging acquisition. For example, the rotational movement configuration in various embodiments includes the number of gantry rotational steps (e.g., as determined at 106 or otherwise). The rotational movement configuration may also specify the size of the steps, and/or an offset or shift for the steps. The rotational movement configuration may be determined, for example, to provide a minimal number of views from the identified detector set for each rotational step, while providing adequate coverage of the ROI. As another example, the rotational movement configuration may be determined to provide a minimal number of views from the identified set of detectors summed over all rotational steps, while providing adequate coverage of the ROI. In various embodiments, the number of views required to provide a desired ROI coverage may be calculated or otherwise determined for a number of rotational movement configurations, with the configuration providing the best number selected.

It may be noted that utilizing a wide coverage as discussed herein may tend to lead toward a relatively larger number of focused long-time projections during the sweeping of some detectors. Further, dividing a set scan time between a larger number of focused projections may result in lower time-per-projection and a related loss of photon counts, lower signal to noise ratio (SNR), and/or reduced image quality. In various embodiments, the gantry position may be shifted to beneficially provide the number of views required to achieve the required ROI coverage. For example, an optimal or improved gantry position may be calculated or determined for a given ROI to provide a reduced or minimal number of views (e.g., for each step or for all steps combined, or a weighted combination of views for each step and total views for all steps combined). Accordingly, a lower scan time may be achieved and/or more time per projection may be employed to improve SNR.

Figure 9:
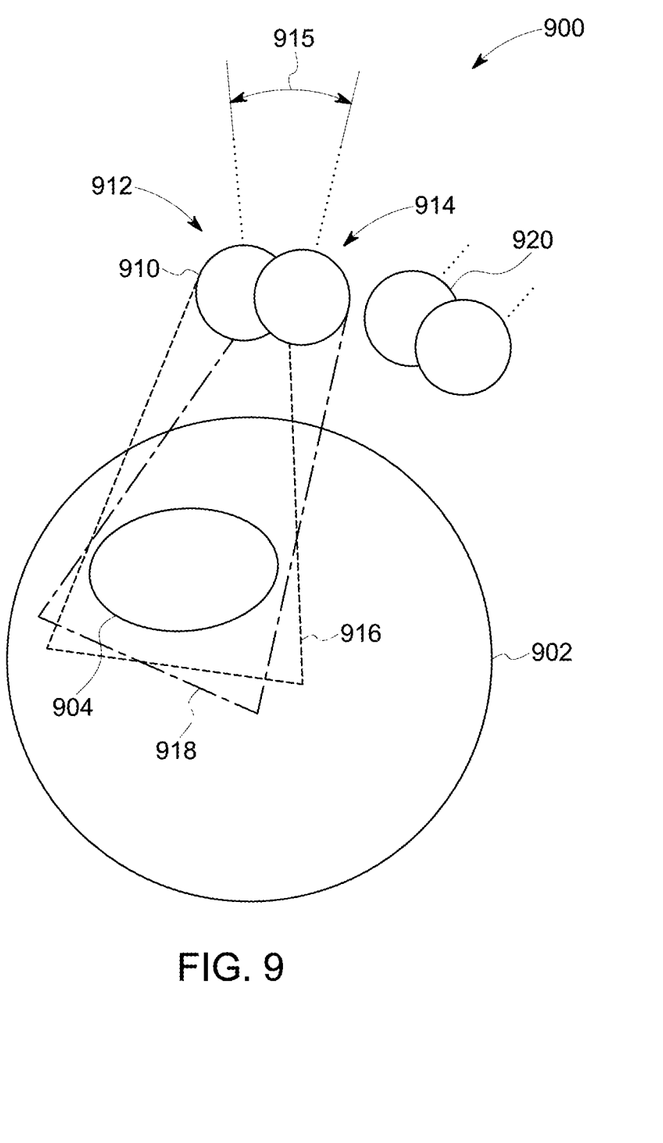
FIG. 9 provides a schematic view of an example detector system, according to an embodiment.

FIG. 9 provides a schematic view of an example detector system 900 having first detector 910 and second detector 920 mounted to a gantry that may be used to image an object 902 having an ROI 904. (It may be noted only two detectors are shown for ease of illustration; however, additional detectors may also be mounted to the gantry.) As seen in FIG. 9, the first detector 910 may have a default position 912, and be shifted by an angle 915 to a shifted position 914. The shifted position 914 provides a different field of view 918 than the field of view 916 corresponding to the default position 912. Depending on the size of the ROI, shape of the ROI, position of the ROI relative to the detectors, or the like, shifting the gantry position may provide a reduced number of views for all detectors combined. For example, the effect of shifting may be determined by determining the required views for the group of detectors at a number of different shift positions, and selecting the shift amount that provides the fewest required views. The shifted position 914 may be used for a first rotational step, with subsequent rotational steps taken at positions a predetermined angular step distance from the first rotational step.

With continued reference to FIG. 1, at 116, a larger percentage of time is spent imaging the ROI to detectors in the identified set relative to detectors not in the identified set. In various embodiments, the detectors selected to the identified set (e.g., at step 108), may be referred to as a primary subset, and have an increased focus time percentage to help avoid reducing time per projection when a wide ROI is desired. However, for the detectors not in the primary subset, more narrow ROI coverage may be allowed, leading to less views for these detectors in the focus ROI and decreased focus percentage (or time spent in focus region or ROI), which allows, for example, spending more time in other regions to help compensate for areas where the detectors in the primary subset spend little or no time (e.g., background, or object boundaries).

The use of different focus percentages (e.g., percentage of time spent on an ROI) may be tailored for particular portions of anatomy. For example, in some scans, the ROI is the striatum. Detectors that are relatively far from the striatum tend to have lower resolution and lower counts than those close to the striatum, with the detectors closer to the striatum having a relatively higher contribution to image quality. Accordingly, those detectors closer to the striatum may be selected as the primary subset, and have a relatively high focus percentage, and used to acquire mainly (or entirely) information from the focus region or ROI, with minimal (or zero) background acquisition. In contrast, those detectors farther from the striatum may be omitted form the primary subset, and used to acquire information from one or more out of focus regions (e.g., portions of the object outside the ROI) to improve background image quality.

It may be noted that the focus criteria or profile may be defined independently for all detectors using a fixed focus or minimal time per projection, allowing flexibility for scanning different object regions.

Returning to FIG. 1, at 118, the gantry and detector units are controlled to acquire imaging information. The determined sweeping configuration and rotational movement configuration define movements of the gantry and detector units, and time spent at each position between which they move, during the acquisition. Accordingly, the gantry and set of detector units are controlled utilizing the determined rotational movement configuration and sweeping configuration during acquisition of imaging information. At 120, an image is reconstructed using the imaging information acquired at 118.

Figure 10:
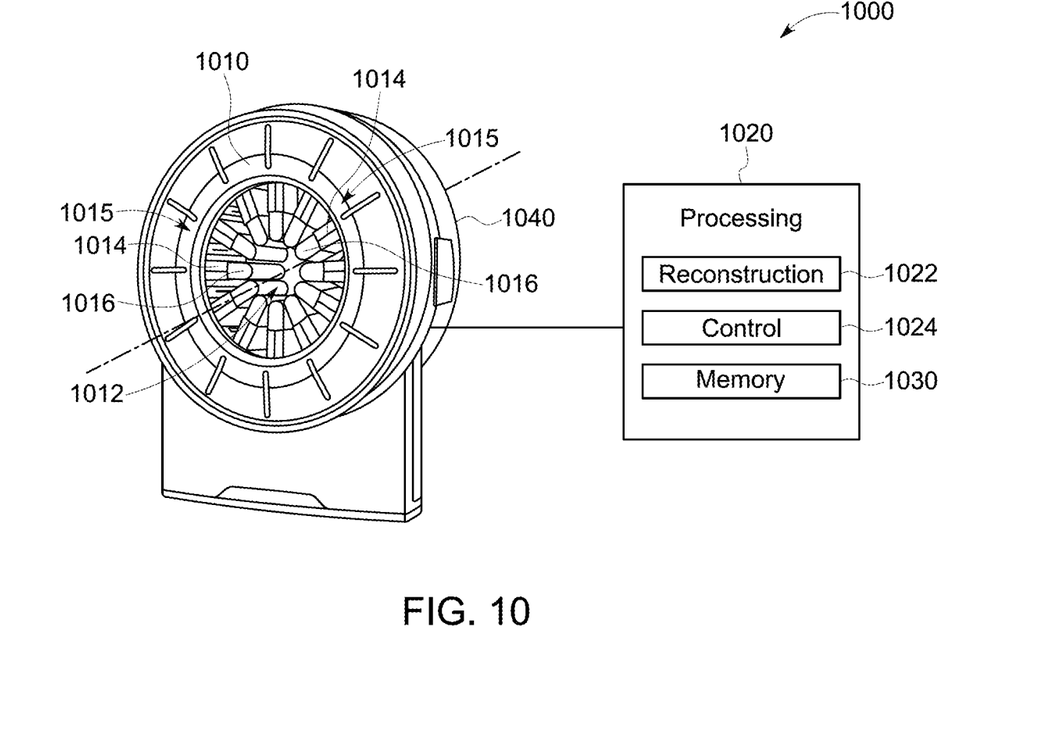
FIG. 10 provides a schematic view of a nuclear medicine (NM) imaging system according to an embodiment.

FIG. 10 provides a schematic view of a nuclear medicine (NM) multi-head imaging system 1000 in accordance with various embodiments. Generally, the imaging system 1000 is configured to acquire imaging information (e.g., photon counts) from an object to be imaged (e.g., a human patient) that has been administered a radiopharmaceutical. The depicted imaging system 1000 includes a gantry 1010 and a processing unit 1020.

The gantry 1010 defines a bore 1012. The bore 1012 is configured to accept an object to be imaged (e.g., a human patient or portion thereof). As seen in FIG. 10, plural detector units 1015 are mounted to the gantry 1010. In the illustrated embodiment, each detector unit 1015 includes an arm 1014 and a head 1016. The arm 1014 is configured to articulate the head 1016 radially toward and/or away from a center of the bore 1012 (and/or in other directions), and the head 1016 includes at least one detector, with the head 1016 disposed at a radially inward end of the arm 1014 and configured to pivot to provide a range of positions from which imaging information is acquired. As discussed above, in various embodiments, the gantry 1010 moves in rotational steps, with the detector units 1015 moving with the gantry 1010 over the rotational steps.

The detector of the head 1016, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. The absorption of photons from certain voxels corresponding to particular pixelated anodes results in charges generated that may be counted. The counts may be correlated to particular locations and used to reconstruct an image.

Figure 11:
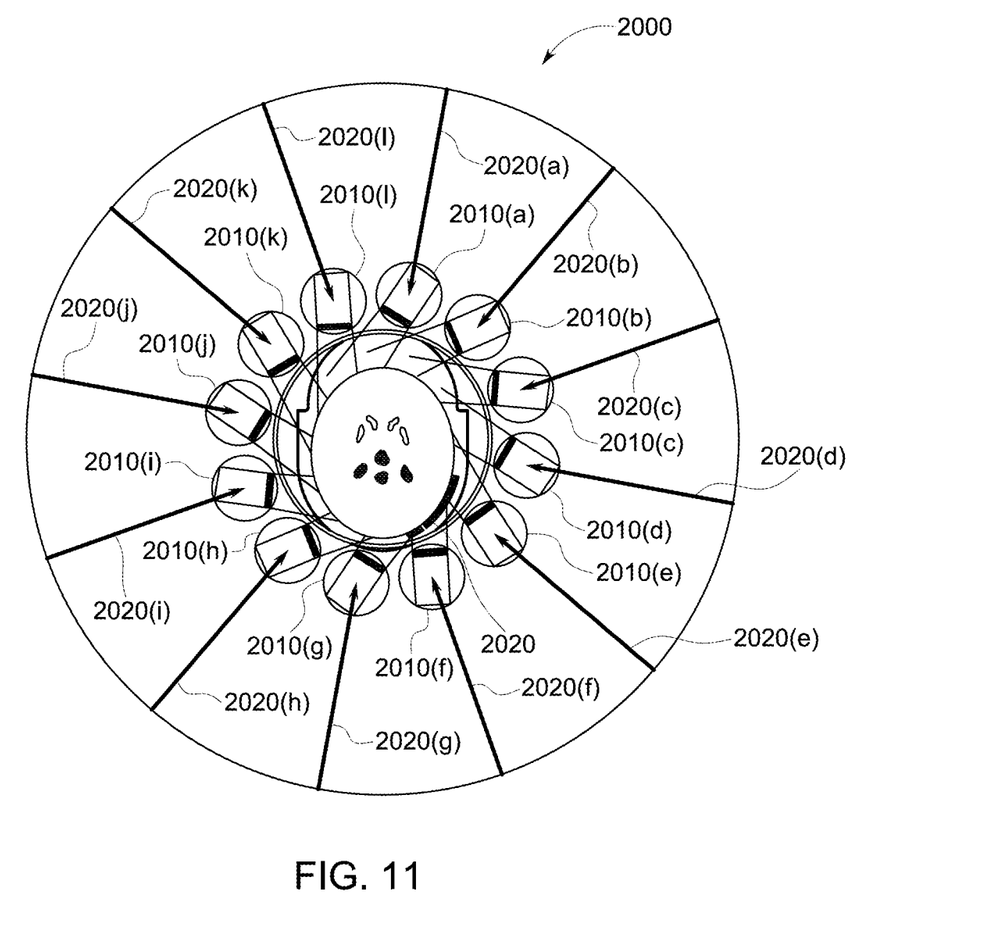
FIG. 11 illustrates a detector arrangement according to an embodiment.

In various embodiments, each detector unit 1015 may define a corresponding view that is oriented toward the center of the bore 1012. Each detector unit 1015 in the illustrated embodiment is configured to acquire imaging information over a sweep range corresponding to the view of the given detector unit. FIG. 11 illustrates a detector arrangement 2000 in accordance with various embodiments. The detector units of FIG. 10, for example, may be arranged in accordance with aspects of the detector arrangement 2000. In some embodiments, the system 1000 further includes a CT (computed tomography) detection unit 1040. The CT detection unit 1040 may be centered about the bore 1012. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 1012.

As seen in FIG. 11, the detector arrangement 2000 includes detector units 2010(*a*), 2010(*b*), 2010(*c*), 2010(*d*), 2010(*e*), 2010(*f*), 2010(*g*), 2010(*h*), 2010(*i*), 2010(*j*), 2010(*k*), 210(*l*) disposed about and oriented toward (e.g., a detection or acquisition surface of the detector units, and/or the FOV (Field Of View), are oriented toward) an object 2002 to be imaged in the center of a bore. Each detector unit of the illustrated embodiment defines a corresponding view that may be oriented toward the center of the bore of the detector arrangement 2000 (it may be noted that because each detector unit may be configured to sweep or rotate about an axis, the FOV need not be oriented precisely toward the center of the bore, or centered about the center of the bore, at all times). The view for each detector unit 2010, for example, may be aligned along a central axis of a corresponding arm (e.g., arm 1014) of the detector unit 2010. In the illustrated embodiment, the detector unit 2010(*a*) defines a corresponding view 2020(*a*), the detector unit 2010(*b*) defines a corresponding view 2020(*b*), the detector unit 2010(*c*) defines a corresponding view 2020(*c*), and so on. The detector units 2010 are configured to sweep or pivot (thus sweeping the corresponding FOV's) over a sweep range (or portion thereof) bounded on either side of a line defined by the corresponding view during acquisition of imaging information. Thus, each detector unit 2010 may collect information over a range larger than a field of view defined by a stationary detector unit. It may be noted that, generally, the sweeping range over which a detector may potentially pivot may be larger than the corresponding view during acquisition. In some cameras, the sweeping range that a detector may pivot may be unlimited (e.g., the detector may pivot a full 360 degrees), while in some embodiments the sweeping range of a detector may be constrained, for example over 180 degrees (from a −90 degree position to a +90 degree position relative to a position oriented toward the center of the bore). It may be noted that the detector units 2010 of FIG. 11 are mounted to a gantry 2030. The gantry 2030 may be rotatable to different positions (e.g., rotational steps), with the detector units 2010 rotating with the gantry 2030. For example, with the gantry 2030 in a first position (e.g., as seen in FIG. 11), the individual detector units 2010 may be swept to acquire a first set or amount of imaging information. Then, the gantry 2030 may be moved to a second position (e.g., rotated to a new position, with the detector units 2010 moving or rotating with the gantry 2030). With the gantry 2030 in the second position, the individual detector units 2010 may be swept again to acquire a second set or amount of imaging information.

With continued reference to FIG. 10, the depicted processing unit 1020 is configured to acquire imaging information via the detector units 1015. In various embodiments as discussed herein, the imaging information acquired by the processing unit 1020 in various embodiments includes focused imaging information (e.g., from the ROI) and background imaging information (from outside the ROI).

In various embodiments the processing unit 1020 includes processing circuitry configured to perform one or more tasks, functions, or steps discussed herein (e.g., to determine sweeping and/or rotational movement configurations, to identify a subset of detectors, to control detectors and/or a gantry to acquire imaging information, and/or to reconstruct an image using acquired imaging information). It may be noted that "processing unit" as used herein is not intended to necessarily be limited to a single processor or computer. For example, the processing unit 1020 may include multiple processors, FPGA's, ASIC's and/or computers, which may be integrated in a common housing or unit, or which may distributed among various units or housings (e.g., one or more aspects of the processing unit 1020 may be disposed onboard one or more detector units, and one or more aspects of the processing unit 1020 may be disposed in a separate physical unit or housing). The processing unit 1020, for example, may control the detector heads to acquire desired amounts of focused and background information, and/or reconstruct an image as discussed herein. It may be noted that operations performed by the processing unit 1020 (e.g., operations corresponding to process flows or methods discussed herein, or aspects thereof) may be sufficiently complex that the operations may not be performed by a human being within a reasonable time period. For example, providing control signals to detector units, reconstructing images, or the like may rely on or utilize computations that may not be completed by a person within a reasonable time period.

In the illustrated embodiment, the processing unit 1020 includes a reconstruction module 1022, a control module 1024, and a memory 1030. It may be noted that other types, numbers, or combinations of modules may be employed in alternate embodiments, and/or various aspects of modules described herein may be utilized in connection with different modules additionally or alternatively. Generally, the various aspects of the processing unit 1020 act individually or cooperatively with other aspects to perform one or more aspects of the methods, steps, or processes discussed herein.

In the illustrated embodiment, the depicted reconstruction module 1022 is configured to reconstruct an image. The depicted control module 1024 is configured to control the detector heads 1016 to sweep over corresponding acquisition ranges to acquiring focused imaging information and background imaging information as discussed herein. It may be noted that, in various embodiments, aspects of the control module 1024 may be distributed among detector units 1015. For example, each detector unit may have a dedicated control module disposed in the head 1016 of the detector unit 1015.

The memory 1030 may include one or more computer readable storage media. The memory 1030, for example, may store information describing previously determined control information (e.g., sweeping configuration, rotational step configuration), parameters to be used for reconstruction (e.g., regularization weight parameter, number of iterations) or the like. Further, the process flows and/or flowcharts discussed herein (or aspects thereof) may represent one or more sets of instructions that are stored in the memory 1030 for direction of operations of the imaging system 1000.

It may be noted that while the processing unit 1020 is depicted schematically in FIG. 10 as separate from the detector units 1015, in various embodiments, one or more aspects of the processing unit 1020 may be shared with the detector units 1015, associated with the detector units 1015, and/or disposed onboard the detector units 1015. For example, in some embodiments, at least a portion of the processing unit 1020 is integrated with at least one of the detector units 1015.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:
   a gantry defining a bore configured to accept an object to be imaged, the gantry configured to rotate about the bore;
   plural detector units mounted to the gantry and configured to rotate as a group with the gantry around the bore in rotational steps, each detector unit configured to sweep about a corresponding axis and acquire imaging information while sweeping about the corresponding axis; and at least one processor operably coupled to at least one of the detector units, the at least one processor configured to:
determine a region of interest (ROI) of the object to be imaged;
determine a sweeping configuration based on the size of the ROI;
determine a rotational movement configuration for the gantry using the determined sweeping configuration; and
control the gantry and the set of detector units to utilize the determined rotational movement and sweeping configurations during acquisition of imaging information.

2. The system of claim 1, wherein the sweeping configuration is determined to result in a predetermined percentage of projection pixels receiving information from the ROI.

3. The system of claim 2, wherein the predetermined percentage varies among at least some of the detector units.

4. The system of claim 1, wherein the at least one processor is configured to acquire a preliminary scan of the ROI, and use the preliminary scan to determine the size of the ROI.

5. The system of claim 1, wherein the at least one processor is configured to receive information from a user corresponding to a boundary of the ROI, and to use the information to determine the size of the ROI.

6. The system of claim 1, wherein the at least one processor is configured to use a predetermined relationship between a number of steps and ROI size to determine the sweeping configuration.

7. The system of claim 6, wherein the at least one processor is configured to use a lookup table to determine a number of rotational steps to be used.

8. The system of claim 1, wherein the at least one processor is configured to determine the rotational movement configuration to provide a minimal number of views for each rotation step.

9. The system of claim 1, wherein the at least one processor is configured to determine the rotational movement configuration to provide a minimal number of views summed over all rotation steps.

10. The system of claim 1, wherein the at least one processor is configured to determine a total number of rotational steps to be taken by the gantry before determining the sweeping configurations.

11. A method for acquiring imaging information with a nuclear medicine (NM) multi-head imaging system comprising a gantry and plural detector units, the gantry defining a bore configured to accept an object to be imaged, the gantry configured to rotate about the bore, the plural detector units mounted to the gantry and configured to rotate as a group with the gantry around the bore, each detector unit configured to sweep about a corresponding axis and acquire imaging information while sweeping about the corresponding axis, the method comprising:
determining a region of interest (ROI) of the object to be imaged;
determining a sweeping configuration using the size of the ROI;
determining a rotational movement configuration for the gantry using the determined sweeping configuration; and
controlling the gantry and the set of detector units to utilize the determined rotational movement and sweeping configurations during acquisition of imaging information.

12. The method of claim 11, further comprising determining the sweeping configuration to result in a predetermined percentage of projection pixels receiving information from the ROI.

13. The method of claim 12, wherein the predetermined percentage varies among at least some of the detector units.

14. The method of claim 11, further comprising acquiring a preliminary scan of the ROI, and using the preliminary scan to determine the size of the ROI.

15. The method of claim 11, further comprising receiving information from a user corresponding to a boundary of the ROI, and using the information to determine the size of the ROI.

16. The method of claim 11, further comprising using a predetermined relationship between a number of steps and ROI size to determine the sweeping configuration.

17. The method of claim 16, further comprising using a lookup table to determine a number of rotational steps to be used.

18. The method of claim 11, further comprising determining the rotational movement configuration to provide a minimal number of views for each rotation step.

19. The method of claim 11, further comprising determining the rotational movement configuration to provide a minimal number of views summed over all rotation steps.

20. The method of claim 11, further comprising determining a total number of rotational steps to be taken by the gantry before determining the sweeping configurations.

* * * * *